United States Patent [19]

Anderson

[11] Patent Number: 4,658,814
[45] Date of Patent: Apr. 21, 1987

[54] ENDOTRACHEAL TUBE HOLDER

[76] Inventor: Kirk D. Anderson, 214 W. Pine St., Eagle River, Wis. 54524

[21] Appl. No.: 729,262

[22] Filed: May 1, 1985

[51] Int. Cl.4 ............................................. A61M 16/00
[52] U.S. Cl. ...................... 128/207.17; 128/DIG. 26; 604/179; 24/115 H; 24/136 R; 24/129 A; 24/122.6
[58] Field of Search ...................... 128/207.17, 207.18, 128/207.14, DIG. 26, 207.15; 604/179; 24/115 H, 115 M, 115 R, 136 R, 122.6, 129 R, 129 A, 129 B, 129 D, 266, 19, 18

[56] References Cited

U.S. PATENT DOCUMENTS

| | | | |
|---|---|---|---|
| 1,146,934 | 7/1915 | Gleeson | 24/129 R |
| 1,442,531 | 1/1923 | Mather et al. | 24/266 |
| 2,100,088 | 11/1937 | Robertson | 24/129 R |
| 3,802,431 | 4/1974 | Farr | 128/207.18 |
| 3,953,144 | 4/1976 | Boden | 24/115 M |
| 4,282,871 | 8/1981 | Chodorow et al. | 128/207.18 |
| 4,316,459 | 2/1982 | Walski | 128/207.17 |
| 4,437,463 | 3/1984 | Ackerman | 128/207.17 |

Primary Examiner—Henry J. Recla
Attorney, Agent, or Firm—Andrus, Sceales, Starke & Sawall

[57] ABSTRACT

An endotracheal tube holder has a cord with a loop through which the endotracheal tube extends. A tube with slits surrounds the cord adjacent the loop to secure the endotracheal tube in the cord when the tube is placed in the mouth and throat of the patient. The remaining portions of the cord extend over the ears and under the chin of the patient. A lockable collar is positioned on the cord to tighten the cord under the chin so as to position and retain the endotracheal tube in the patient.

11 Claims, 5 Drawing Figures

ENDOTRACHEAL TUBE HOLDER

The present invention relates to a holder for positioning and retaining an endotracheal tube in a patient.

An endotracheal tube is inserted through the mouth and throat of a patient to provide an airway for breathing. To insure that the tube is retained in the proper position in the patient's throat, some means for securing the endotracheal tube must be provided.

A common practice is to simply secure the endotracheal tube to the patient's face with adhesive tape. However, this is not entirely satisfactory. For long term intubation, the tape must usually be repeatedly removed and reapplied. This becomes very painful to the patient. Also, the tape may impede the drainage of body fluids such as saliva, sputum, blood, or vomit from the oral cavity. The presence of the body fluids may also prevent satisfactory adhering of the tape to the skin.

It is, therefore, the object of the present invention to provide an improved holding means for positioning and retaining an endotracheal tube in the mouth and throat of a patient.

Briefly, the holder of the present invention includes a cord having some degree of elasticity. The cord has a loop in the central portion through which the endotracheal tube extends. Means are provided for securing the loop about the endotracheal tube. The central portion of the cord is positioned adjacent the lips of the patient when the endotracheal tube is in the mouth. The remaining portions of the cord extend over the ears and under the chin of the patient. Means are provided for retaining the ends of the cord under the chin of the patient to hold the endotracheal tube in the mouth. A spacer may be provided between the loop and the endotracheal tube to permit the drainage of body fluids.

The endotracheal tube holder of the present invention is further explained in the following detailed description with the aid of the drawing in which.

Figure 1:
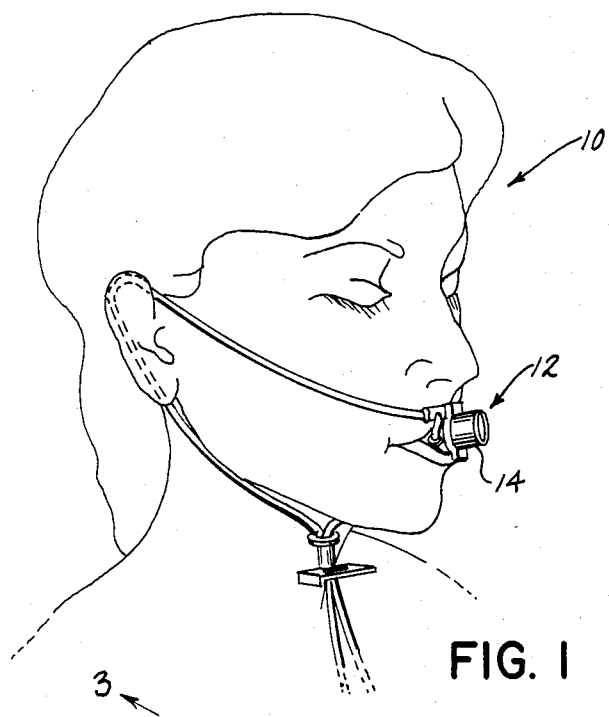
FIG. 1 is a perspective view of the endotracheal tube holder of the present invention in use on a patient.
Figure 2:
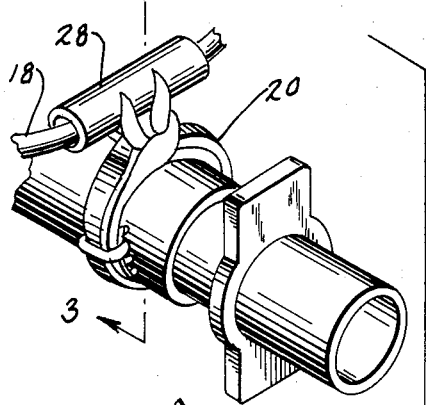
FIG. 2 is a perspective view of the holder of the present invention and the associated portions of the endotracheal tube.

FIG. 1 shows patient 10 intubated with endotracheal tube 12. An end 14 of endotracheal tube 12 extends from the mouth of the patient to receive air or respiratory therapy apparatus.

The endotracheal tube holder 16 of the present invention includes cord 18. Cord 18 is preferably formed of tubing, such as surgical tubing or that commonly used in connection with intravenous feeding bottles. Such tubing possesses some elastic properties. A loop 20 is formed in the central portion of cord 18. The loop may be formed by folding cord 18 in half, placing the portion of the cord adjacent the fold around endotracheal tube 12 and inside the fold, as shown most clearly in FIGS. 3 and 5.

Figure 3:
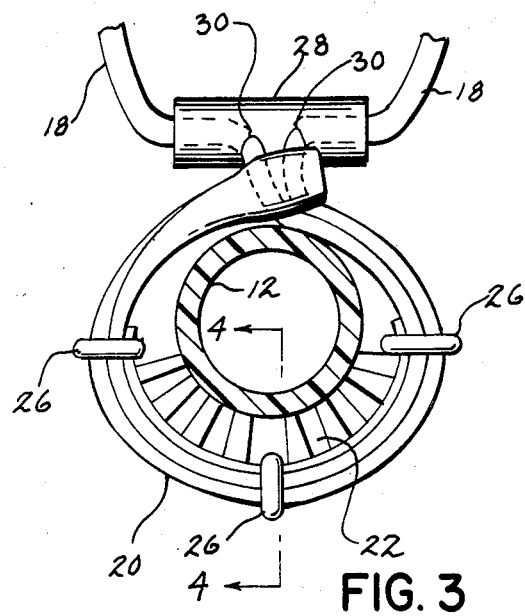
FIG. 3 is a cross-sectional view taken along the line 3—3 of FIG. 2.
Figure 4:
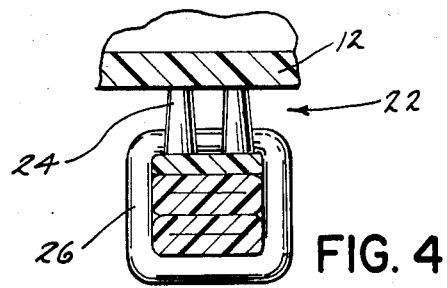
FIG. 4 is a cross-sectional view taken along the line 4—4 of FIG. 3.
Figure 5:
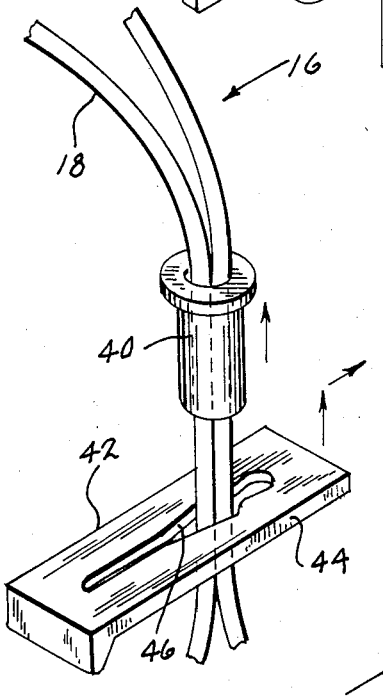
FIG. 5 is a cross-sectional view, similar to FIG. 3 showing another embodiment of the present invention.
Figure 5:
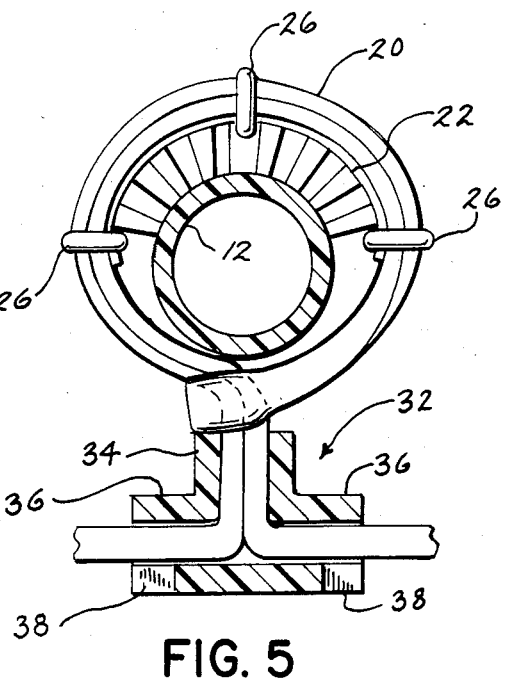

In a preferred embodiment of the invention, spacer 22 is provided between the inside of loop 20 and the exterior of endotracheal tube 12 to permit the drainage of fluids away from the lip area of the patient and so that they do not collect on the exterior of the tube. As shown in FIGS. 3, 4, and 5, spacer 22 may comprise a comb-like structure having teeth 24 that grip the exterior of endotracheal tube 12 at spaced intervals. Spacer 22 may be fastened to loop 20 by bands 26. Or, spacer 22 may be glued or welded to cord 18 or teeth 24 may be molded with cord 18 as a single unit.

Means are employed for selectively securing endotracheal tube 12 in loop 20. A resilient cylinder 28 contains a pair of transverse slits 30. One portion of cord 18 extends through one slit 30 and out one end of the cylinder while the other portion extends through the other slit 30 and out the other end of the cylinder. Cylinder 28 is bent in an upwardly opening U-shape when oriented as in FIG. 3 to move it along cord 18. In the straight condition, shown in FIG. 3, cylinder 28 locks on cord 18 so as to secure endotracheal tube 12 in loop 20 when cylinder 28 is moved into proximity with the loop. The securing means, such as cylinder 28, usually lies on top of the endotracheal tube beneath the nose of the patient, as shown in FIG. 1. The configuration of cylinder 28 is particularly convenient for placement beneath the nose of the patient.

FIG. 5 shows another form of the securing means. Device 32 is formed as a hollow, resilient, T-shaped member having a stem 34 through which both portions of cord 18 extend and a pair of transverse arms 36 through each of which one of the portions of card 18 extend. Device 32 may be bent to permit it to move along the portions of cord 18. Slits 38 may be provided in arms 36 to lock the portions of the cord in device 32 when placed in the slits.

The portions of cord 18 exiting the securing means extend along either side of the face of patient 10, over the ears, and under the chin. Collar 40 surrounds portions and is placed snugly under the chin. A lock 42 retains the collar in place on the portions of the cord. Lock 42 may comprise plate 44 having a wedge-shaped slot 46.

The endotracheal tube holder of the present invention provides a rapid, easy means for positioning and retaining the endotracheal tube in the patient. It can be applied without going under the neck of the patient or otherwise moving the patient. This is particularly advantageous in connection with patients having apparent or suspected neck or spinal cord injuries. Fluid discharges do not collect on the exterior of the tube or compromise the certainty with which the tube is positioned and retained.

Various modes of carrying out the invention are contemplated as being within the scope of the following claims particularly pointing out and distinctly claiming the subject matter which is regarded as the invention.

I claim:

1. An improved holding means for positioning and retaining an endotracheal tube in the mouth and throat of a patient comprising:
    a cord having a loop in a generally central portion thereof through which the endotracheal tube extends, said loop being formed by placing said central portion of said cord around the endotracheal tube;
    means for securing said loop about the endotracheal tube for retaining the endotracheal tube in said loop,
    said central portion of said cord being positioned adjacent the lips of the patient when the endotracheal tube is in the mouth and throat of the patient, the remaining portions of said cord extending over the ears and under the chin of the patient; and means for retaining the remaining portions of the cord under the chin of the patient to hold the endotracheal tube in the mouth of he patient, said securing means comprising a flexible cylinder having a pair of spaced slits in which the portions of the cord adjacent said loop enter the cylinder, the remaining portions of said cord exiting the cylinder at opposite ends.

2. The endotracheal tube holding means according to claim 1 wherein said cord is a cord having elastic properties.

3. The endotracheal tube holding means according to claim 2 wherein said cord comprises surgical tubing.

4. The endotracheal tube holding means according to claim 1 wherein said loop is formed by folding the cord in half in the central portion thereof, placing the portion of the cord adjacent the fold around the endotracheal tube and through the inside of the fold, and wherein said securing means surrounds the porions of the cord outside said loop.

5. The endotracheal tube holding means according to claim 1 wherein said means for retaining the remaining portions of the cord under the chin of the patient include a collar surrounding said remaining portions and means for locking said collar in a desired position on said remaining portions.

6. An improved holding means for positioning and retaining an endotracheal tube in the mouth and throat of a patient comprising:

a cord having a loop in a generally central portion thereof through which the endotracheal tube extends;

means for securing said loop about the endotracheal tube for retaining the endotracheal tube in said loop, said central portion of said cord being positioned adjacent the lips of the patient when the endotracheal tube is in the mouth and throat of the patient, the remaining portions of said cord extending over the ears and under the chin of the patient; and means for retaining the remaining portions of the cord under the chin of the patient to hold the endotracheal tube in the mouth of the patient, said securing means being T-shaped with a hollow stem adjacent said loop and surrounding a part of the remaining portions of said cord, said securing means having hollow arms transverse to said stem through each of which one of the remaining portions of said cord extends in opposing directions.

7. The endotracheal tube holding means according to claim 6 wherein said arms of said T-shaped securing means contain slits in which said remaining portions of said cord may be placed for retaining same in said securing means.

8. An improved holding means for positioning and retaining an endotracheal tube in the mouth and throat of a patient comprising:

a cord having a loop in a generally central portion thereof through which the endotracheal tube extends;

means for securing said loop about the endotracheal tube for retaining the endotracheal tube in said loop, said central portion of said cord being positioned adjacent the lips of the patient when the endotracheal tube is in the mouth and throat of the patient, the remaining portions of said cord extending over the ears and under the chin of the patient;

means for retaining the remaining portions of the cord under the chin of the patient to hold the endotracheal tube in the mouth of the patient and, means for spacing all portions of said loop in said cord except in sections adjacent said securing means from the exterior of the endotracheal tube to permit the drainage of fluids away from the lip area of the patient and so that they do not collect on the exterior of the tube.

9. The endotracheal tube holding means according to claim 8 wherein said spacing means is formed to permit the passage of fluid.

10. The endotracheal tube holding means according to claim 8 wherein said spacing means includes grips at spaced intervals.

11. The endotracheal tube holding means according to claim 8 wherein said spacing means has a comb like structure.

* * * * *